US011161787B2

(12) United States Patent
Tajika et al.

(10) Patent No.: US 11,161,787 B2
(45) Date of Patent: Nov. 2, 2021

(54) HIGH-PURITY CALCIUM CARBONATE SINTERED BODY AND PRODUCTION METHOD THEREOF, AND HIGH-PURITY CALCIUM CARBONATE POROUS SINTERED BODY AND PRODUCTION METHOD THEREOF

(71) Applicants: SHIRAISHI CENTRAL LABORATORIES CO. LTD., Amagasaki (JP); NATIONAL UNIVERSITY CORPORATION YAMAGATA UNIVERSITY, Yamagata (JP)

(72) Inventors: Masahiko Tajika, Amagasaki (JP); Shota Umemoto, Amagasaki (JP); Hidero Unuma, Yonezawa (JP); Jun Ito, Yonezawa (JP)

(73) Assignees: SHIRAISHI CENTRAL LABORATORIES CO., LTD., Amagasaki (JP); NATIONAL UNIVERSITY CORPORATION YAMAGATA UNIVERSITY, Yamagata (JP)

( * ) Notice: Subject to any disclaimer, the term of this patent is extended or adjusted under 35 U.S.C. 154(b) by 0 days.

(21) Appl. No.: 16/487,556

(22) PCT Filed: Feb. 26, 2018

(86) PCT No.: PCT/JP2018/006917

§ 371 (c)(1),
(2) Date: Aug. 21, 2019

(87) PCT Pub. No.: WO2018/155680

PCT Pub. Date: Aug. 30, 2018

(65) Prior Publication Data

US 2019/0375687 A1 Dec. 12, 2019

(30) Foreign Application Priority Data

Feb. 27, 2017 (JP) .............................. JP2017-035245

(51) Int. Cl.
 *C04B 35/057* (2006.01)
 *C04B 35/64* (2006.01)
 *C04B 38/10* (2006.01)

(52) U.S. Cl.
 CPC ............ *C04B 35/057* (2013.01); *C04B 35/64* (2013.01); *C04B 38/10* (2013.01); *C04B 2235/3208* (2013.01)

(58) Field of Classification Search
 CPC ....... C04B 35/057; C04B 35/64; C04B 38/10; C04B 38/00; C04B 2235/32
 See application file for complete search history.

(56) References Cited

U.S. PATENT DOCUMENTS

| 5,187,125 A * | 2/1993 | Someya ................. C04B 35/03 106/35 |
| 2013/0224421 A1* | 8/2013 | Kamei ................... C04B 35/04 428/64.1 |

(Continued)

FOREIGN PATENT DOCUMENTS

| CN | 104876641 A | 9/2015 |
| CN | 105503107 A | 4/2016 |

(Continued)

OTHER PUBLICATIONS

Tomatsuri et al., "Effect of Starting Materials on Liquid Phase Sintering of Calcium Carbonate", Proceedings for the Academic Conference of the Society of Inorganic Materials, Japan, Nov. 14, 2002, vol. 105, pp. 46-47, cited in Specification (2 pages).

(Continued)

*Primary Examiner* — Noah S Wiese
(74) *Attorney, Agent, or Firm* — Westerman, Hattori, Daniels & Adrian, LLP

(57) ABSTRACT

A high-purity calcium carbonate sintered body containing less impurities and available for biological and like applications, a production method, a high-purity calcium carbon- (Continued)

ate porous sintered body containing less impurities and available for biological and like applications, and a production method. A method for producing a high-purity calcium carbonate sintered body includes the steps of: compaction molding calcium carbonate with a purity of 99.7% by mass or more to make a green body; and sintering the green body to produce a calcium carbonate sintered body. A method for producing a high-purity calcium carbonate porous sintered body according to the present invention includes the steps of: preparing a dispersion liquid containing calcium carbonate with a purity of 99.7% by mass or more; adding a foaming agent to the dispersion liquid, followed by stirring until foamy to make a foam; and sintering the foam to produce a calcium carbonate porous sintered body.

13 Claims, 2 Drawing Sheets

(56) References Cited

U.S. PATENT DOCUMENTS

| | | | | |
|---|---|---|---|---|
| 2015/0295160 A1* | 10/2015 | Oshima | ............... | C04B 35/6342 347/68 |
| 2016/0204335 A1* | 7/2016 | Oshima | ................. | H02N 2/001 347/68 |

FOREIGN PATENT DOCUMENTS

| | | | | |
|---|---|---|---|---|
| CN | 106116687 | A | 11/2016 | |
| DE | 19507309 | A1 * | 9/1995 | ............. C04B 35/64 |
| EP | 3 466 902 | A1 | 4/2019 | |
| JP | 62-36021 | A | 2/1987 | |
| JP | 04-231367 | A * | 8/1992 | ............. C04B 35/02 |
| JP | 4-231367 | A | 8/1992 | |
| JP | 5-310469 | A | 11/1993 | |
| JP | 7-242415 | A | 9/1995 | |
| JP | 8-198623 | A | 8/1996 | |
| JP | 2007-254240 | A | 10/2007 | |
| JP | 2011-251886 | A | 12/2011 | |
| JP | 2012-240872 | A | 12/2012 | |
| JP | 2017-214237 | A | 12/2017 | |
| JP | 2017-214238 | A | 12/2017 | |

OTHER PUBLICATIONS

International Search Report dated May 1, 2018, issued in counterpart International Application No. PCT/JP2018/006917 (2 pages).
Notification of Transmittal of Translation of the International Preliminary Report on Patentability (Form PCT/IB/338) issued in counterpart International Application No. PCT/JP2018/006917 dated Sep. 6, 2019 with Forms PCT/IB/373 and PCT/ISA/237. (9 pages).
European Search Report dated Nov. 20, 2020, issued in counterpart EP Application No. 18758072.5. (11 pages).
Tetard et al., "Pre-Eutectic Densification of Calcium Carbonate Doped with Lithium Carbonate", Journal of Thermal Analysis and Calorimetry, vol. 56, No. 3, Jun. 1, 1999, pp. 1461-1473. Cited in European Search Report dated Nov. 20, 2020. (13 pages).
Ito et al., "Preparation and properties of pressureless-sintered dense calcite ceramics", Materials Chemistry and Physics, vol. 192, May 1, 2017, pp. 304-310. Cited in European Search Report dated Nov. 20, 2020. ( 7 pages).
Vlasov et al., "Science for Ceramic Production Sintering of Calcium Carbonate in the Presence of Lithium Carbonate Additive", Jan. 1, 1997, pp. 11-12. Cited in European Search Report dated Nov. 20, 2020. (3 pages).
Chroscicka et al., "Synthetic Calcite as a Scaffold for Osteoinductive Bone Substitutes", Annals of Biomedical Engineering, vol. 44, No. 7, Jul. 2016, pp. 2145-2157. Cited in European Search Report dated Nov. 20, 2020. ( 13 pages).
Maruta et al., "Fabrication of low-crystalline carbonate apatite foam bone replacement based on phase transformation of calcite foam", Dental Materials Journal, vol. 30, No. 1, Jan. 1, 2011, pp. 14-20. Cited in European Search Report dated Nov. 20, 2020. ( 7 pages).
Office Action dated Jul. 13, 2021, issued in counterpart CN Application No. 201880013576 8, with English translation. (16 pages).

* cited by examiner

[FIG. 1]
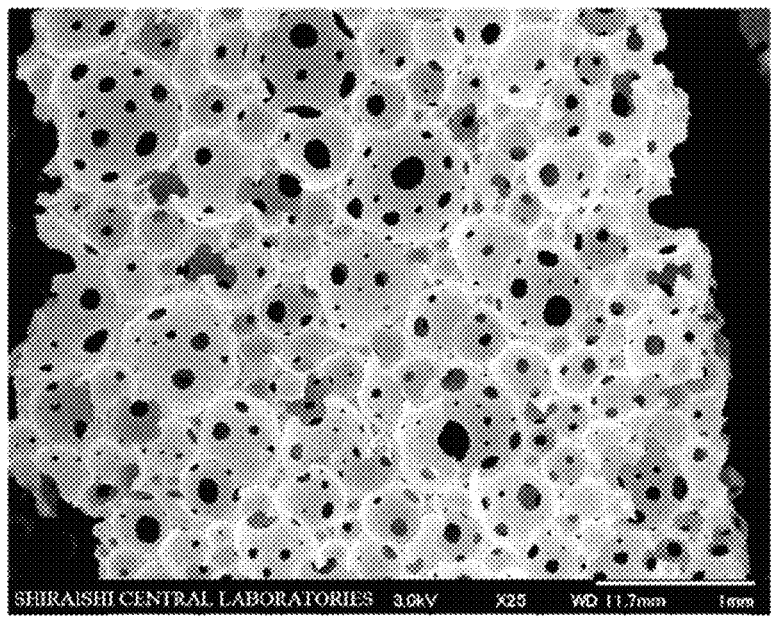
[FIG. 2]
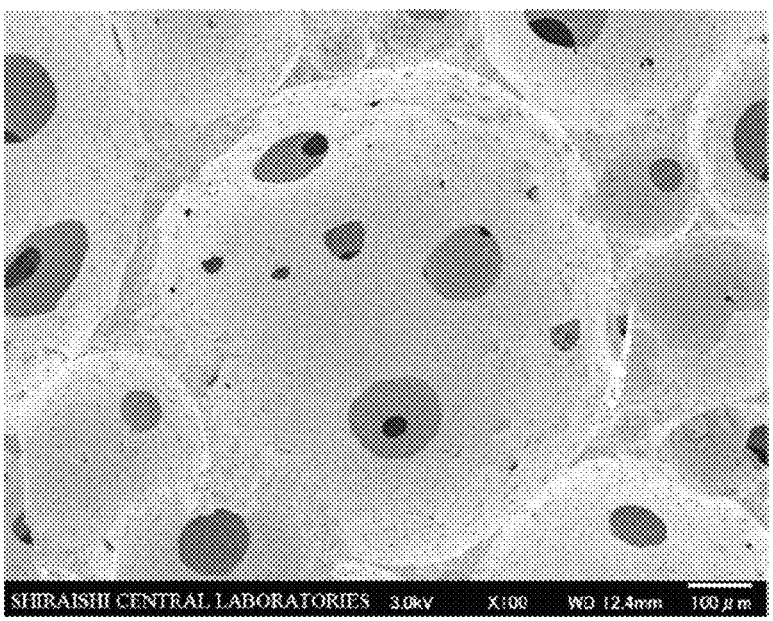

[FIG. 3]
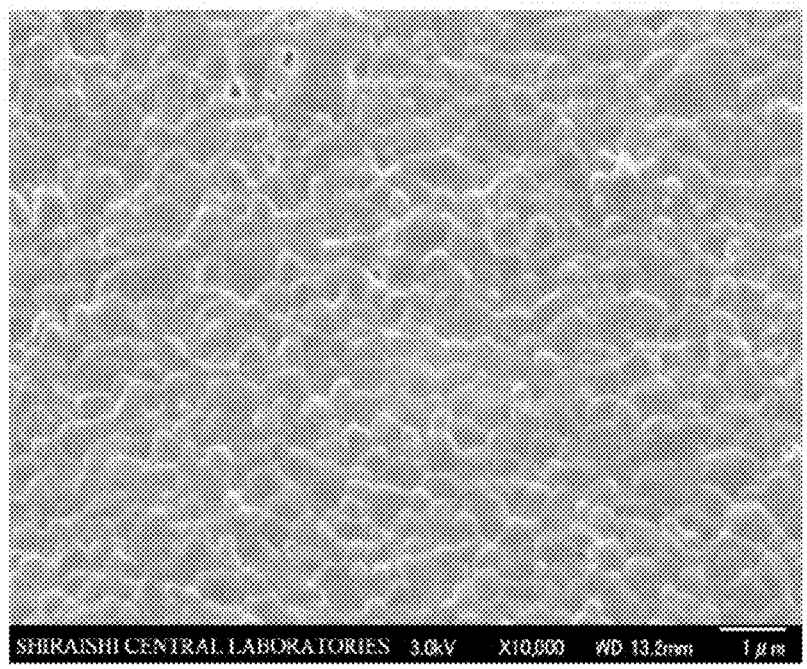
[FIG. 4]
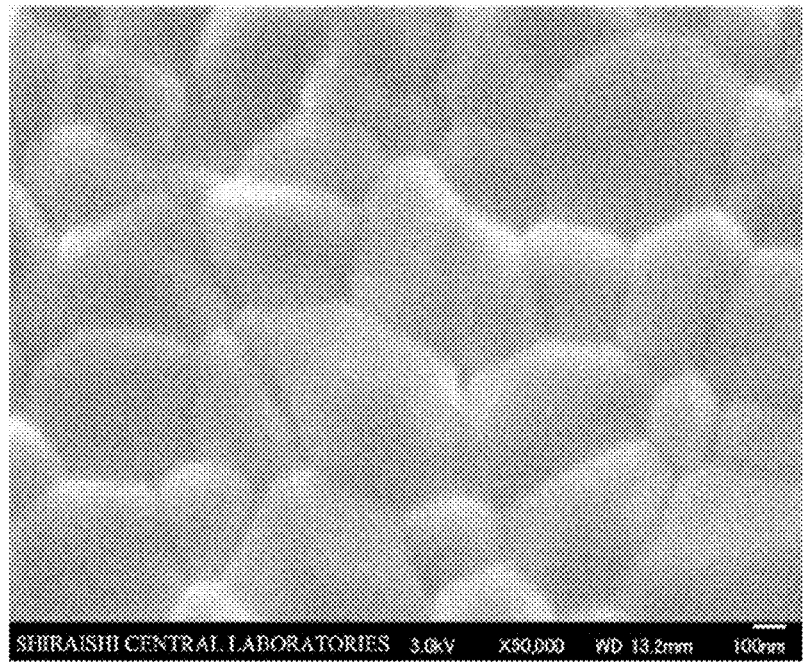

HIGH-PURITY CALCIUM CARBONATE SINTERED BODY AND PRODUCTION METHOD THEREOF, AND HIGH-PURITY CALCIUM CARBONATE POROUS SINTERED BODY AND PRODUCTION METHOD THEREOF

TECHNICAL FIELD

The present invention relates to high-purity calcium carbonate sintered bodies and production methods thereof, and high-purity calcium carbonate porous sintered bodies and production methods thereof.

BACKGROUND ART

A calcium carbonate sintered body is expected to be applied to a growth nucleus for an artificial pearl, a biological body, and so on, and various studies have been done on its production method. In conventional methods for producing a calcium carbonate sintered body, generally, a calcium carbonate sintered body is produced by isostatically pressing a mixture of calcium carbonate and a sintering aid into a green body and sintering this green body in a carbon dioxide atmosphere (see Patent Literature 1 and Non-Patent Literature 1).

CITATION LIST

Patent Literature

Patent Literature 1: JP-A-2007-254240
Non-Patent Literature 1: Satoko Tomatsuri et al., "Effect of Starting Materials on Liquid Phase Sintering of Calcium Carbonate", Proceedings for the Academic Conference of the Society of Inorganic Materials, Japan, Vol. 105th, p. 46-47 (Nov. 14, 2002)

SUMMARY OF INVENTION

Technical Problem

However, a conventional calcium carbonate sintered body requires a sintering aid as described above, which makes it difficult to reduce the content of impurities in the conventional calcium carbonate sintered body. For this reason, the conventional calcium carbonate sintered body may not be available for biological and like applications.

An object of the present invention is to provide a high-purity calcium carbonate sintered body containing less impurities and available for biological and like applications, a production method thereof, and provide a high-purity calcium carbonate porous sintered body containing less impurities and available for biological and like applications, and a production method thereof.

Solution to Problem

A high-purity calcium carbonate sintered body according to the present invention contains 99.7% by mass or more calcium carbonate and has a relative density of 90% or more.

A method for producing a high-purity calcium carbonate sintered body according to the present invention includes the steps of: compaction molding calcium carbonate with a purity of 99.7% by mass or more to make a green body; and sintering the green body to produce a calcium carbonate sintered body.

In the method for producing a high-purity calcium carbonate sintered body according to the present invention, the green body preferably contains calcium carbonate only.

In the method for producing a high-purity calcium carbonate sintered body according to the present invention, the green body is preferably sintered at 420 to 600° C.

In the method for producing a high-purity calcium carbonate sintered body according to the present invention, the compaction molding is preferably uniaxial molding.

In the method for producing a high-purity calcium carbonate sintered body according to the present invention, the green body is preferably sintered in air.

A high-purity calcium carbonate porous sintered body according to the present invention contains 99.7% by mass or more calcium carbonate and has a porosity of 50% by volume or more.

The high-purity calcium carbonate porous sintered body according to the present invention preferably contains 99.9% by mass or more calcium carbonate.

In the high-purity calcium carbonate porous sintered body according to the present invention, a connected pore leading to an exterior of the sintered body is preferably formed.

A method for producing a high-purity calcium carbonate porous sintered body according to the present invention includes the steps of: preparing a dispersion liquid containing calcium carbonate with a purity of 99.7% by mass or more; adding a foaming agent to the dispersion liquid, followed by stirring until foamy to make a foam; and sintering the foam to produce a calcium carbonate porous sintered body.

In the method for producing a high-purity calcium carbonate porous sintered body according to the present invention, the foam is preferably freeze-dried and then sintered.

In the method for producing a high-purity calcium carbonate porous sintered body according to the present invention, the dispersion liquid preferably contains the calcium carbonate in an amount of 20% by volume or more.

In the method for producing a high-purity calcium carbonate porous sintered body according to the present invention, the step of sintering is preferably the step of performing presintering and then performing final sintering. In this case, the temperature of the presintering is preferably in a range of 200 to 500° C. and the temperature of the final sintering is preferably equal to or more than the temperature of the presintering and in a range of 420 to 600° C.

Calcium carbonate for producing a high-purity calcium carbonate sintered body according to the present invention has a purity of 99.9% by mass or more.

Calcium carbonate for producing a high-purity calcium carbonate porous sintered body according to the present invention has a purity of 99.9% by mass or more.

Advantageous Effects of Invention

The high-purity calcium carbonate sintered body according to the present invention contains less impurities and is also available for biological and like applications.

The method for producing a high-purity calcium carbonate sintered body according to the present invention enables less use of sintering aid and therefore enables the production of a high-purity calcium carbonate sintered body containing less impurities.

The high-purity calcium carbonate porous sintered body according to the present invention contains less impurities and is also available for biological and like applications.

The method for producing a high-purity calcium carbonate porous sintered body according to the present invention enables less use of sintering aid and therefore enables the production of a high-purity calcium carbonate porous sintered body containing less impurities.

BRIEF DESCRIPTION OF DRAWINGS

FIG. 1 is a scanning electron micrograph (at 25-fold magnification) showing a high-purity calcium carbonate porous sintered body of Example 3.

FIG. 2 is a scanning electron micrograph (at 100-fold magnification) showing the high-purity calcium carbonate porous sintered body of Example 3.

FIG. 3 is a scanning electron micrograph (at 10000-fold magnification) showing the high-purity calcium carbonate porous sintered body of Example 3.

FIG. 4 is a scanning electron micrograph (at 50000-fold magnification) showing the high-purity calcium carbonate porous sintered body of Example 3.

DESCRIPTION OF EMBODIMENTS

Hereinafter, a description will be given of preferred embodiments. However, the following embodiments are merely illustrative and the present invention is not limited to the following embodiments.

<High-Purity Calcium Carbonate Sintered Body>

(Calcium Carbonate)

Calcium carbonate for use in the present invention is preferably one having a purity of 99.7% by mass or more, more preferably having a purity of 99.9% by mass or more, and still more preferably having a purity of 99.95% by mass or more. Such high-purity calcium carbonate can be produced, for example, by the method disclosed in Japanese Patent Application Gazette No. 2012-240872. With the use of high-purity calcium carbonate, the amount of sintering aid necessary for sintering can be small. Alternatively, a sintered body of calcium carbonate can be produced without sintering aid.

Although no particular limitation is placed on the upper limit of the purity of calcium carbonate, it is generally 99.9999% by mass.

In relation to calcium carbonate for use in the present invention, the average particle diameter ($D_{50}$) in the particle diameter distribution measured by transmission electron microscope observation is preferably in a range of 0.05 to 0.5 μm, more preferably in a range of 0.08 to 0.3 μm, and still more preferably in a range of 0.1 to 0.25 μm. When the average particle diameter ($D_{50}$) is in the above range, a high-density green body can be made, so that a high-purity calcium carbonate sintered body having a high density can be produced. The particle diameter distribution by transmission electron microscope observation can be obtained by measuring 1000 or more particles of calcium carbonate, which is an object to be measured, by transmission electron microscope observation.

The BET specific surface area of calcium carbonate for use in the present invention is preferably 5 to 25 $m^2/g$, more preferably 7 to 20 $m^2/g$, and still more preferably 8 to 15 $m^2/g$. When the BET specific surface area is in the above range, the sinterability of calcium carbonate can be increased. Thus, a high-purity calcium carbonate sintered body having a high density can be produced.

(Sintering Aid)

With the use of high-purity calcium carbonate in accordance with the present invention, the amount of sintering aid necessary for sintering can be small. Alternatively, a sintered body of calcium carbonate can be produced without sintering aid. Therefore, according to the present invention, the content of calcium carbonate in the sintered body can be increased, so that a high-purity calcium carbonate sintered body can be produced.

However, as necessary, a sintering aid may be used. Examples of the sintering aid include those containing at least two of carbonates of lithium, sodium, and potassium and having a melting point of 600° C. or below. The melting point of the sintering aid is preferably 550° C. or below, more preferably 530° C. or below, and still more preferably in a range of 450 to 520° C. When the melting point of the sintering aid is in the above range, a calcium carbonate green body can be fired at a lower temperature to produce a calcium carbonate sintered body. Because in the sintering the sintering aid is used by addition to calcium carbonate, the actual melting point becomes lower than the above temperature and, therefore, it sufficiently acts as a sintering aid. The sintering aid is preferably a mixture of potassium carbonate and lithium carbonate. For example, the melting point of the sintering aid can be determined from a phase diagram or can be measured by differential thermal analysis (DTA).

Alternatively, a mixture of potassium fluoride, lithium fluoride, and sodium fluoride may be used as the sintering aid. Such a mixture also preferably has the above range of melting points. Examples of such a sintering aid include mixtures having a composition range of 10 to 60% by mole potassium fluoride, 30 to 60% by mole lithium fluoride, and 0 to 30% by mole sodium fluoride. Within the above range, a calcium carbonate green body can be fired at a lower temperature and a higher-density calcium carbonate sintered body can be produced.

In using a sintering aid, a mixture of calcium carbonate and the sintering aid is preferably prepared by mixing calcium carbonate with the sintering aid so that the content of the sintering aid in the mixture is 1.5% by mass or less, more preferably 1.0% by mass or less, and still more preferably 0.7% by mass or less. If the content of the sintering aid is too large, the purity and density of the calcium carbonate sintered body may not be able to be increased.

With the use of high-purity calcium carbonate in accordance with the present invention, the sintering temperature can be decreased as compared to the case of use of calcium carbonate not having a high purity.

(Sintering Temperature)

The sintering temperature is preferably 600° C. or below, more preferably 580° C. or below, and still more preferably 560° C. or below. If the sintering temperature is too high, calcium carbonate is likely to decompose to generate calcium oxide, which is undesirable. The sintering temperature is preferably not less than 420° C., more preferably not less than 430° C., and still more preferably not less than 440° C. If the sintering temperature is too low, calcium carbonate may not sufficiently be sintered.

(Green Body)

In the present invention, calcium carbonate powder only or a mixture of calcium carbonate powder and a sintering aid is compaction-molded to make a green body. The compaction molding is preferably uniaxial molding. According to the present invention, using a green body made by uniaxial molding, a high-purity calcium carbonate sintered body having a high density can be produced. However, in the present invention, the making of a green body is not limited to uniaxial molding and a green body may be made by any other known forming method, such as isostatic pressing, doctor blade technique or casting.

In the present invention, the relative density of the green body is preferably 50% or more, more preferably 55% or more, and still more preferably 58% or more. The relative density of the green body is a value obtained by dividing the bulk density of the green body by the theoretical density (2.711 g/cm$^3$) of calcium carbonate. The bulk density of the green body can be measured by the Archimedes's method to be described later. The relative density of the green body is preferably that obtained when the mixture is uniaxially pressed at a molding pressure of 196.1 Mpa (2000 kgf/cm$^2$). Within the above range of relative densities, a high-purity calcium carbonate sintered body having a higher density can be obtained.

(Production of Calcium Carbonate Sintered Body)

In the present invention, a calcium carbonate sintered body can be produced by sintering the above green body. From the viewpoint of sintering in a simpler process, the atmosphere during the sintering is preferably in air. However, the present invention is not limited to this and the green body may be sintered, as with the conventional techniques, in a carbon dioxide atmosphere or in an atmosphere of inert gas, such as nitrogen gas. According to the present invention, even by sintering in air, a high-purity calcium carbonate sintered body having a high density can be produced. The sintering temperature is preferably in the above range.

Alternatively, in the present invention, the green body may be sintered by irradiating it with laser light. Furthermore, the green body may be sintered by irradiating it with laser light using a 3D printer.

The relative density of the calcium carbonate sintered body is preferably 90% or more, more preferably 95% or more, still more preferably 97% or more, yet still more preferably 98% or more, and particularly preferably 99% or more.

The purity of the calcium carbonate sintered body is preferably 99.7% by mass or more, more preferably 99.8% by mass or more, still more preferably 99.9% by mass or more, yet still more preferably 99.95% by mass or more, and particularly preferably 99.99% by mass or more. Thus, the calcium carbonate sintered body also becomes available for biological and like applications. Although no particular limitation is placed on the upper limit of the purity of the calcium carbonate sintered body, it is generally 99.9999% by mass.

<High-Purity Calcium Carbonate Porous Sintered Body>

(Calcium Carbonate)

As calcium carbonate, calcium carbonate described in the above production of a high-purity calcium carbonate sintered body can be used. Also in the production of a calcium carbonate porous sintered body, with the use of high-purity calcium carbonate, the amount of sintering aid necessary for sintering can be small. Alternatively, a porous sintered body of calcium carbonate can be produced without sintering aid. In using a sintering aid, the same type and content of sintering aid as described above can be selected.

(Foaming Agent)

Examples of a foaming agent to be used in the present invention include alkyl sulfate ester salts, such as triethanolamine lauryl sulfate, polyoxyethylene alkyl ether sulfate ester salts, polyoxyethylene alkyl ether acetates, and alkyl polyglucoside.

(Excipient)

In the present invention, an excipient may be added into a dispersion liquid. The addition of an excipient can increase the strength of bubbles in a dispersion foam obtained after foaming to stabilize the shape of the foam. Examples of the excipient include starch, dextrin, polyvinyl alcohol, polypropylene glycol, pectine, alginic acids, and sodium salts of carboxy cellulose.

(Dispersion Liquid)

In the present invention, calcium carbonate is preferably dispersed into a dispersion medium using a device having a high stirring force, such as a disperser, a mixer or a ball mill, while gradually adding calcium carbonate into the dispersion medium, such as water. The content of calcium carbonate is generally preferably 30 to 70% by mass in the dispersion liquid. In doing so, if necessary, about 0 to about 3 parts by mass of polymeric surfactant, such as a polyacrylate, may be added as a dispersant to 100 parts by mass of calcium carbonate.

(Making of Foam)

In the present invention, a foaming agent is added to the above dispersion liquid and the mixture is then stirred until foamy, thus making a foam. The addition of the foaming agent is preferably performed so that the concentration of the foaming agent in the dispersion liquid reaches about 0.01 to about 5% by mass. The stirring is preferably performed with a handheld mixer, a disperser or the like. When the stirring is performed, the temperature of the dispersion liquid may increase. If necessary, the stirring may be performed while the dispersion liquid is cooled.

(Freeze-Drying)

In the present invention, the above foam is preferably freeze-dried and then sintered. By the freeze-drying, the shape of the foam can be easily maintained, so that a porous sintered body can be obtained in a good shape.

Specifically, it is preferred that the foam should be preliminarily frozen at −40° C. or below under ordinary pressure for two or more hours and then gradually increased in temperature under reduced pressure while its ice crystals are sublimated. The condition of the reduced pressure is preferably at 20 Pa or less and more preferably at 10 Pa or less. The temperature is preferably gradually increased while the reduced pressure is maintained without melting the ice crystals, and the temperature is generally controlled in a range of −40° C. to 60° C.

(Sintering of Foam)

In the present invention, a calcium carbonate porous sintered body can be produced by sintering the foam. In the present invention, the foam is preferably presintered and then finally sintered. Thus, it can be prevented that organic components contained in the foam remain and become carbonized and darkened or the organic components rapidly decompose to create cracks in the sintered body.

The temperature of the presintering is preferably in a range of 200 to 500° C. and more preferably in a range of 300 to 420° C. The temperature of the final sintering is preferably equal to or more than the temperature of the presintering and in a range of 420 to 600° C., and more preferably in a range of 450 to 540° C.

Furthermore, the rate of temperature increase during the presintering and the final sintering is preferably in a range of 2° C. to 20° C. per minute. Thus, it can be prevented that the organic components rapidly decompose to create cracks in the sintered body.

The atmosphere during the sintering is preferably in air. However, the present invention is not limited to this and the foam may be sintered in a carbon dioxide atmosphere or in an atmosphere of inert gas, such as nitrogen gas. According to the present invention, even by sintering in air, a high-purity calcium carbonate porous sintered body can be produced.

(Calcium Carbonate Porous Sintered Body)

The high-purity calcium carbonate porous sintered body according to the present invention contains 99.7% by mass or more calcium carbonate and has a porosity of 50% by volume or more.

The purity of the calcium carbonate porous sintered body is preferably 99.7% by mass or more, more preferably 99.8% by mass or more, still more preferably 99.9% by mass or more, yet still more preferably 99.95% by mass or more, and particularly preferably 99.99% by mass or more. Thus, the calcium carbonate porous sintered body also becomes available for biological and like applications. Although no particular limitation is placed on the upper limit of the purity of the calcium carbonate porous sintered body, it is generally 99.9999% by mass.

The porosity of the calcium carbonate porous sintered body is preferably 50% by volume or more, more preferably 60% by volume or more, still more preferably 70% by volume or more, yet still more preferably 80% by volume or more, and particularly preferably 85% by volume or more. Thus, the calcium carbonate porous sintered body also becomes available for biological and like applications. Although no particular limitation is placed on the upper limit of the porosity of the calcium carbonate porous sintered body, it is generally 95% by volume.

In the high-purity calcium carbonate porous sintered body according to the present invention, a connected pore leading to the exterior of the sintered body is preferably formed. Thus, calcium carbonate inside the porous sintered body can be easily brought into contact with the external atmosphere. Therefore, the calcium carbonate porous sintered body can be more suitably used, for example, in biological and like applications.

EXAMPLES

Hereinafter, a description will be given of specific examples according to the present invention, but the present invention is not limited to the following examples.

Production of Calcium Carbonate Sintered Body

Example 1

(Calcium Carbonate)

Calcium carbonate having a purity of 99.99% by mass, an average particle diameter ($D_{50}$) of 0.15 μm, and a BET specific surface area of 10 m$^2$/g was used. The purity was derived by the difference method. Specifically, the respective amounts of impurities in a sample liquid for measurement obtained by dissolving a sample having a known mass were measured with an inductively coupled plasma emission spectrometer, the sum of the measurement results was considered as the content of impurities, and a value obtained by subtracting the content of impurities from the total mass was defined as the purity.

The average particle diameter ($D_{50}$) was determined by measuring the particle diameters of 1500 particles of calcium carbonate, which is an object to be measured, by transmission electron microscope observation and using the obtained particle diameter distribution.

The BET specific surface area was measured by the single point method using FlowSorb 2200 manufactured by Shimadzu Corporation.

Using the above-described calcium carbonate, a calcium carbonate sintered body was produced in the following manner.

(Making of Green Body)

Calcium carbonate was put into a polyethylene bottle containing a suitable amount of zirconia balls and dry mixed overnight to obtain a raw material powder. This raw material powder was put into a cylindrical mold and uniaxially pressed using a press. The raw material powder was preliminarily pressed at a molding pressure of 98 Mpa (1000 kgf/cm$^2$) for one minute and then pressed at a molding pressure of 196.1 Mpa (2000 kgf/cm$^2$) for one minute.

(Firing of Green Body)

The obtained green body was fired at a firing temperature of 540° C. in air for three hours to sinter it. Note that until the firing temperature was reached, the temperature was increased at a rate of 10° C. per minute. By the firing, a calcium carbonate sintered body was obtained.

(Measurement of Relative Density of Calcium Carbonate Sintered Body)

The bulk density $\rho_b$ [g/cm$^3$] of the calcium carbonate sintered body was obtained by the Archimedes's method and the obtained bulk density was divided by the theoretical density (2.711 g/cm$^3$) of calcium carbonate to obtain its relative density. The bulk density of the calcium carbonate sintered body was obtained as follows. First, the dry weight $W_1$ of a sample of the calcium carbonate sintered body was measured, the sample was allowed to stand for about 10 minutes in paraffin warmed in a vessel put in hot water, then picked up, and cooled to ordinary temperature. After the sample was cooled, the weight $W_2$ of the sample containing paraffin was measured. Thereafter, the weight $W_3$ of the sample in water was measured and the bulk density $\rho_b$ of the sample was then determined from the following equation. The relative density of the calcium carbonate sintered body is shown in Table 1.

$$\text{Bulk Density } \rho_b[\text{g/cm}^3] = W_1 \rho_w / (W_2 - W_3)$$

$\rho_w$: water density [g/cm$^3$]

$W_1$: dry weight [g] of sample $W_2$: weight [g] of sample containing paraffin $W_3$: weight [g] of sample in water (Measurement of Purity of Calcium Carbonate Sintered Body)

The purity of the calcium carbonate sintered body was derived by the above-described difference method.

The purity of the calcium carbonate sintered body is shown in Table 1.

Example 2

A calcium carbonate sintered body was produced in the same manner as in Example 1 except that calcium carbonate having a purity of 99.91% by mass, an average particle diameter ($D_{50}$) of 0.15 μm, and a BET specific surface area of 10 m$^2$/g was used. The relative density and purity of the calcium carbonate sintered body are shown in Table 1.

Comparative Example 1

An attempt was made to produce a calcium carbonate sintered body in the same manner as in Example 1 except that calcium carbonate having a purity of 99.61% by mass, an average particle diameter ($D_{50}$) of 0.15 μm, and a BET specific surface area of 10 m$^2$/g was used. However, a green body of calcium carbonate could not be sintered.

Comparative Example 2

Calcium carbonate in Comparative Example 1 and a sintering aid were mixed so that the content of the sintering aid reached 0.7% by mass, and the mixed powder was dry mixed in the manner described above to prepare a raw material powder. A calcium carbonate sintered body was produced in the same manner as in Example 1 except that the raw material powder was used.

A mixture of potassium carbonate and lithium carbonate was used as the sintering aid. The mixing ratio was, in terms of molar ratio, potassium carbonate to lithium carbonate=38:62. The melting point (eutectic temperature) of the mixture was 488° C. The relative density and purity of the calcium carbonate sintered body are shown in Table 1.

TABLE 1

|  | Calcium Carbonate | | | | Calcium Carbonate Sintered Body | |
| --- | --- | --- | --- | --- | --- | --- |
|  | Purity (% by mass) | Average Particle Diameter $D_{50}$(μm) | BET Specific Surface Area (m$^2$/g) | Sintering Aid | Purity (% by mass) | Relative Density (%) |
| Ex. 1 | 99.99 | 0.15 | 10 | Not contained | 99.99 | 97.0 |
| Ex. 2 | 99.91 | 0.15 | 10 | Not contained | 99.9 | 94.0 |
| Comp. Ex. 1 | 99.61 | 0.15 | 10 | Not contained | 99.6 | 68.0 |
| Comp. Ex. 2 | 99.61 | 0.15 | 10 | Contained | 98.8 | 93.0 |

As shown in Table 1, in Examples 1 and 2 according to the present invention, high-purity calcium carbonate sintered bodies were obtained which contained more than 99.7% by mass calcium carbonate and had a relative density of more than 90%. In contrast, in Comparative Example 1 in which calcium carbonate with a purity of less than 99.7% by mass was used, the relative density was 68.0% and a calcium carbonate sintered body was not obtained. Even with the use of calcium carbonate having a purity of less than 99.7% by mass, a calcium carbonate sintered body could be produced by using a sintering aid as shown in Comparative Example 2. However, because of addition of the sintering aid, the content of calcium carbonate decreased, so that the calcium carbonate sintered body could not be a high-purity calcium carbonate sintered body.

Production of Calcium Carbonate Porous Sintered Body

Example 3

Pure water was put into a polyethylene bottle containing a suitable amount of zirconia balls and the same calcium carbonate as used in Example 1 was added into the pure water to reach 39% by volume. Next, 0.8 parts by mass of polyvinyl alcohol as an excipient and 2.5 parts by mass of polymeric surfactant as a dispersant (special polycarboxylate polymer type surfactant under the trade name of "POIZ 520" manufactured by Kao Corporation) were added to 100 parts by mass of calcium carbonate and the mixture was then wet mixed for 12 hours using a pot mill. A 19% by mass aqueous solution of polyoxyethylene alkyl ether as a foaming agent was added to the obtained slurry to reach 2 ml per 10 g of slurry, thus preparing a dispersion liquid.

The dispersion liquid was foamed with a handheld mixer to obtain a foam. The obtained foam was poured into a mold and freeze-dried in this state. The freeze-drying was performed under the conditions that the foam was preliminarily frozen at −40° C. under ordinary pressure for 12 hours and then held at 30° C. under a reduced pressure of 10 Pa for 48 hours.

The freeze-dried foam was increased in temperature at a rate of 10° C. per minute until a presintering temperature (350° C.) and presintered for 10 hours after the temperature increase. After having been cooled, the foam was increased in temperature at the same rate of temperature increase until a final sintering temperature (510° C.) and finally sintered for three hours after the temperature increase, thus obtaining a calcium carbonate porous sintered body.

The purity and porosity of the obtained calcium carbonate porous sintered body are shown in Table 2. The purity was measured in the same method as done for the calcium carbonate sintered body. The porosity was obtained by cutting the sintered body into a rectangular block, determining the density of the block from the weight and apparent volume of the block, dividing the density by the true density of calcium carbonate, 2.711 g/cm$^3$, to obtain a relative density, and defining as a porosity the value obtained by subtracting the relative density from the entirety.

Example 4

A calcium carbonate porous sintered body was produced in the same manner as in Example 3 except that the same calcium carbonate as used in Example 2 was used. The purity and porosity of the calcium carbonate porous sintered body are shown in Table 2.

Comparative Example 3

An attempt was made to produce a calcium carbonate porous sintered body in the same manner as in Example 3 except that the same calcium carbonate as used in Comparative Example 1 was used. However, a foam could not be sintered.

TABLE 2

| | Calcium Carbonate | | | | Calcium Carbonate Porous Sintered Body | |
|---|---|---|---|---|---|---|
| | Purity (% by mass) | Average Particle Diameter $D_{50}(\mu m)$ | BET Specific Surface Area $(m^2/g)$ | Sintering Aid | Purity (% by mass) | Porosity (%) |
| Ex. 3 | 99.99 | 0.15 | 10 | Not contained | 99.9 | 89.0 |
| Ex. 4 | 99.91 | 0.15 | 10 | Not contained | 99.8 | 88.3 |
| Comp. Ex. 3 | 99.61 | 0.15 | 10 | Not contained | — | — |

As shown in Table 2, in Examples 3 and 4 according to the present invention, high-purity calcium carbonate porous sintered bodies were obtained which contained more than 99.7% by mass calcium carbonate and had a porosity of more than 50% by volume. In contrast, in Comparative Example 3 in which calcium carbonate with a purity of less than 99.7% by mass was used, a calcium carbonate porous sintered body was not obtained.

<Scanning Electron Microscope Observation of Calcium Carbonate Porous Sintered Body>

FIGS. 1 to 4 are scanning electron micrographs of the calcium carbonate porous sintered body obtained in Example 3. FIG. 1 is a micrograph at 25-fold magnification, FIG. 2 is one at 100-fold magnification, FIG. 3 is one at 10000-fold magnification, and FIG. 4 is one at 50000-fold magnification. As is obvious from FIGS. 1 and 2, it can be seen that the calcium carbonate porous sintered body had connected pores leading to the exterior of the sintered body. Furthermore, as is obvious from FIGS. 3 and 4, it can be seen that calcium carbonate particles were densely sintered to form a porous sintered body.

The invention claimed is:

1. A method for producing a high-purity calcium carbonate sintered body, the method comprising the steps of:
   compaction molding calcium carbonate with a purity of 99.91% by mass or more and an average particle diameter ($D_{50}$) in a range of 0.05 to 0.3 μm to make a green body without using a sintering aid; and
   sintering the green body to produce a calcium carbonate sintered body having a relative density of 90% or more.

2. The method for producing a high-purity calcium carbonate sintered body according to claim 1, wherein the green body contains calcium carbonate only.

3. The method for producing a high-purity calcium carbonate sintered body according to claim 1, wherein the green body is sintered at 420 to 600° C.

4. The method for producing a high-purity calcium carbonate sintered body according to claim 1, wherein the compaction molding is uniaxial molding.

5. The method for producing a high-purity calcium carbonate sintered body according to claim 1, wherein the green body is sintered in air.

6. A high-purity calcium carbonate porous sintered body containing 99.7% by mass or more calcium carbonate and having a porosity of 50% by volume or more.

7. The high-purity calcium carbonate porous sintered body according to claim 6, containing 99.9% by mass or more calcium carbonate.

8. The high-purity calcium carbonate porous sintered body according to claim 6, wherein a connected pore leading to an exterior of the sintered body is formed.

9. A method for producing a high-purity calcium carbonate porous sintered body, the method comprising the steps of:
   preparing a dispersion liquid containing calcium carbonate with a purity of 99.7% by mass or more;
   adding a foaming agent to the dispersion liquid, followed by stirring until foamy to make a foam; and
   sintering the foam to produce a calcium carbonate porous sintered body.

10. The method for producing a high-purity calcium carbonate porous sintered body according to claim 9, wherein the foam is freeze-dried and then sintered.

11. The method for producing a high-purity calcium carbonate porous sintered body according to claim 9, wherein the dispersion liquid contains the calcium carbonate in an amount of 20% by volume or more.

12. The method for producing a high-purity calcium carbonate porous sintered body according to claim 9, wherein the step of sintering is the step of performing presintering and then performing final sintering.

13. The method for producing a high-purity calcium carbonate porous sintered body according to claim 12, wherein a temperature of the presintering is in a range of 200 to 500° C. and a temperature of the final sintering is equal to or more than the temperature of the presintering and in a range of 420 to 600° C.

* * * * *